US008877127B2

(12) United States Patent
Buri et al.

(10) Patent No.: US 8,877,127 B2
(45) Date of Patent: Nov. 4, 2014

(54) PROCESS FOR CONTROL OF MICROBIAL CONTAMINATION, MINERAL SUSPENSIONS OBTAINED AND THEIR USES

(71) Applicants: Matthias Buri, Rothrist (CH); Patrick Schwarzentruber, Boppelsen (CH); Silvia Hub-Schmid, Olten (CH)

(72) Inventors: Matthias Buri, Rothrist (CH); Patrick Schwarzentruber, Boppelsen (CH); Silvia Hub-Schmid, Olten (CH)

(73) Assignee: Omya International AG, Ofringen (CH)

( * ) Notice: Subject to any disclaimer, the term of this patent is extended or adjusted under 35 U.S.C. 154(b) by 0 days.

(21) Appl. No.: 14/011,971

(22) Filed: Aug. 28, 2013

(65) Prior Publication Data

US 2014/0000486 A1    Jan. 2, 2014

Related U.S. Application Data

(63) Continuation of application No. 11/794,511, filed as application No. PCT/IB2006/000151 on Jan. 20, 2006.

(30) Foreign Application Priority Data

Jan. 26, 2005   (FR) ..................................... 05 00779

(51) Int. Cl.
| A61L 2/16 | (2006.01) |
| B01J 13/00 | (2006.01) |
| A61L 2/18 | (2006.01) |
| C09D 7/12 | (2006.01) |

(52) U.S. Cl.
CPC ........... C09D 7/1216 (2013.01); B01J 13/0008 (2013.01); A61L 2/18 (2013.01); A61L 2/16 (2013.01); B01J 13/0039 (2013.01); B01J 13/0086 (2013.01)
USPC ........................................... 422/28; 106/464

(58) Field of Classification Search
CPC .......... C09D 7/1216; A61L 2/16; A61L 2/18; B01J 13/0008; B01J 13/00039; B01J 13/0086
USPC ........ 422/28; 106/464; 514/769; 516/98, 110
See application file for complete search history.

(56) References Cited

U.S. PATENT DOCUMENTS

| 3,659,708 A | 5/1972 | Morris et al. |
| 5,167,707 A | 12/1992 | Freeman et al. |
| 5,432,238 A | 7/1995 | Egraz et al. |
| 5,569,702 A | 10/1996 | Egraz et al. |
| 5,736,601 A | 4/1998 | Egraz et al. |
| 6,602,484 B1 | 8/2003 | Virtanen |
| 6,756,437 B1 | 6/2004 | Xue et al. |
| 2001/0008877 A1 | 7/2001 | Hartman et al. |
| 2002/0088566 A1* | 7/2002 | Doelle .............................. 162/9 |
| 2003/0012685 A1 | 1/2003 | Wachtler et al. |
| 2004/0023929 A1 | 2/2004 | Larson et al. |
| 2004/0023939 A1* | 2/2004 | Buri et al. ...................... 514/184 |
| 2005/0006041 A1* | 1/2005 | Gane et al. .................... 162/135 |
| 2007/0027294 A1 | 2/2007 | Murao et al. |

FOREIGN PATENT DOCUMENTS

| DE | 4233600 C1 | 3/1994 |
| DE | 19811742 A1 | 9/1999 |
| DE | 10027588 A1 | 12/2000 |
| EP | 0398487 A1 | 11/1990 |
| EP | 0850283 | 7/1998 |
| FR | 2683539 | 5/1993 |
| JP | 2004169243 A | 6/2004 |
| JP | 09020629 A | 1/2009 |
| WO | 9816471 A1 | 4/1998 |
| WO | 0046392 A2 | 8/2000 |
| WO | 0185659 A1 | 11/2001 |
| WO | 0213774 A2 | 2/2002 |
| WO | 2005108866 A1 | 11/2005 |

OTHER PUBLICATIONS

English language abstract of Nagasawa et al., "Disinfection Characteristics of Lime Compounds", J Soc Inorg Mater Jpn (2002) 9 492-497.*
The English Translation of the Office Action dated Jul. 3, 2012 for related Japanese Application No. 2007-552746.

* cited by examiner

*Primary Examiner* — Timothy Cleveland
(74) *Attorney, Agent, or Firm* — Aster, Rothstein & Ebenstein LLP

(57) ABSTRACT

The invention concerns a process for disinfection and/or conservation and/or reduction and/or control of microbial contamination of aqueous dispersions and/or aqueous suspensions of mineral matter, providing satisfactory stability in terms of Brookfield™ viscosity for the said aqueous dispersions and/or suspensions of mineral matter. It also concerns the said aqueous dispersions and/or suspensions thus obtained, together with their uses in the mineral, paper and paint industries. Finally it concerns the end products obtained.

17 Claims, No Drawings

PROCESS FOR CONTROL OF MICROBIAL CONTAMINATION, MINERAL SUSPENSIONS OBTAINED AND THEIR USES

CROSS-REFERENCE TO RELATED APPLICATIONS

This is continuation of U.S. application Ser. No. 11/794,511, filed Jun. 27, 2007, which is a U.S. national phase of PCT Application No. PCT/IB2006/000151, filed Jan. 20, 2006, which claims priority to French Application No. FR0500779, filed Jan. 26, 2005, the contents of which is hereby incorporated by reference.

The invention concerns in the first instance a process for disinfection and/or conservation and/or reduction and/or control of microbial contamination of aqueous dispersions and/or aqueous suspensions of mineral matter, providing satisfactory stability in terms of Brookfield™ viscosity for the said aqueous dispersions and/or suspensions of mineral matter.

Another purpose of the invention lies in aqueous suspensions and/or dispersions of mineral matter, having satisfactory stability in terms of Brookfield™ viscosity and having a very small number of microbial germs and/or of which the concentration of microbial germs can be controlled by means of the process according to the invention, Another purpose of the invention consists in the use of the said aqueous suspensions and/or dispersions of mineral matter in the mineral industry, in the paper industry, preferably in the manufacture of paper, and/or in paper coating, and also in the field of manufacture of water-based paints, and notably lacquers and varnishes.

A final purpose of the invention lies in mineral formulations, paper formulations and notably paper sheets and coating colours, water-based paints, lacquers and varnishes characterised in that they contain the said aqueous suspensions and/or dispersions of mineral matter according to the invention.

A first object of the invention is thus a process for disinfection and/or conservation and/or reduction and/or control of microbial contamination of suspensions and/or of aqueous dispersions of minerals and/or of fillers and/or of pigments, for protection faced with microbial contamination and/or deliberate control of the growth of a microorganism during the preparation of the said dispersions and/or suspensions, of their storage, of their transport, and at the time of their modification and/or treatment over an interval of time which may be determined by the user. The process is preferably used in mines, in the paper industry and in the varnishes and paints industry.

The aim of the process is essentially to reduce the concentration of and/or to avoid traditional biocides as, notably, specified in "XXXVI Empfehlung" vom BgVV (Bundesinstitut für gesundheitlichen Verbraucherschutz und Vetrinärmedizin, Deutschland) in "Kunststoffe im Lebensmittelverkehr" Carl Heymanns Verlag kg, Köln, Berlin, Bonn, Munich and in Federal Code 21 §176.300, revision of 1 Apr. 2001. As a consequence it reduces the risks of contamination and poisoning for humans, and of damage to the environment when such biocides were used according to the prior art, alone, and in generally high concentrations.

Another aim is to create a process incorporating a time interval, which may be chosen freely, during which the system must act.

Another major aim is not to influence, or, if this were to be unavoidable, to influence in a positive manner, the properties of the processed products and/or their subsequent use.

Another aim is to combine such a treatment in the habitual stages of manufacture of minerals and/or pigments and/or fillers such as, notably, the common stages of dispersion and/or grinding in water of the said fillers.

A final aim is to provide a process which does not modify the long-term stability of the Brookfield™ viscosity of the aqueous suspensions and dispersions of mineral matter thus obtained.

In the present application, the following is designated through the term "microbes": every organism and/or microorganism, aerobic or anaerobic, of a bacterial nature, such as bacterial germs, and notably mesophilic aerobic bacterial germs, such as *pseudomonas aeruginosa, salmonella enteritidis* and *escherichia coli*, as gram-negative representatives, and *bacillus subtilis, staphylococcus aureus, listeria monocytogenes* and *micrococcus luteus*, as gram-positive representatives, but also anaerobic bacterial germs and anaerobic sulphate reducing bacterial germs, such as *desulfovibrio desuifaricans*, but also fungi, and notably *aspergillus niger*, together with yeasts, and notably *saccharomyces cerevisiae*.

Through the expression "disinfection and/or preservation" it is also understood that water and/or aqueous solutions and/or aqueous suspensions and/or aqueous dispersions containing mineral matter are protected against a microbial attack and/or are protected against a risk of microbial infection, principally by prevention of growth and/or by destruction of the said microbes.

These notions of disinfection and of preservation thus cover all the curative and protective effects in terms of protection of the said aqueous suspensions and/or dispersions of mineral matter in relation to a microbial attack.

Finally, the terms "dispersions" and "suspensions" of mineral matter refer in the present application to a composition containing water, mineral matter the concentration by dry weight of which is greater than or equal to 0.1% relative to the total weight of the said dispersions and suspensions, and possibly other additives such as notably dispersing agents, grinding aid agents and anti-foaming agents.

Currently, to accomplish disinfection and protection of water and/or aqueous solutions and/or aqueous suspensions and/or aqueous dispersions containing mineral matter, the skilled man in the art has two types of solutions, which he may use alone or in combination: the use of organic chemicals referred to under the term biocides, or the use of treatment processes not involving these biocides. The Applicant will now present the state of the technique relative to both these approaches, whilst highlighting the disadvantages constituted by all these current solutions.

Aqueous dispersions and suspensions of minerals and/or fillers and/or pigments are habitually conserved using biocides which can be applied individually or in combination. Habitual substances with a biocidal effect for use in aqueous suspensions and/or aqueous dispersions of mineral matter and in industrial circuit water are, notably, listed in the Code of Federal Regulations 21, §170 to §199, modified in April 2000, section 176.300, Slimicides. Such substances are also covered in the work "Praxis der Sterilisation, Desinfektion-Konservierung" by Karl Heinz Wallhausser, completely revised $5^{th}$ edition published by Georg Thieme Verlag, Stuttgart and in the document "Microbicides for the protection of materials, a handbook by Wilfried Paulus" first edition 1993, published by Chapman & Hall, 2-6 Boundary Row, London SE1 8HN. In addition in the "Code of Federal Regulation 21, §170 to §199, modified in April 2001, such substances with biocidal effects are described in sections 176.170 and 176.300".

Among the widely used biocidal formulations, some contain 1.2 benzisothiazoline-3-on. The disadvantage of such formulations it is what is called a "pseudomonas window", i.e. the substance has a biocidal effect against many bacteria but nevertheless has a lesser effectiveness against certain bacteria, in this instance the pseudomonas. Moreover, this substance causes cutaneous sensitisation and is consequently dangerous for the users. Another disadvantage lies in the stability of the said product, such that during a subsequent application the bactericidal effect of 1.2 benzisothiazoline-3-on is not cancelled and it can then influence food products by traversing packaging substances for such products and/or utility objects for food products. In addition, the poor degradability of this compound and its strong toxicity have a destructive effect on the environment in the event that the said product migrates through the packaging containing it, or in the event of degradation of the said packaging.

Moreover, the skilled man in the art can also use mixtures of 5-chloro-2-methyl-4-isothiazolinon and 2-methyl-4-isothiazolinon. Here, the disadvantage lies in the fact that only 5-chloro-2-methyl-4-isothiazolinon manifests a sufficient efficacy relative to bacteria; and this substance is very unstable when exposed to alkaline pH values and to heat, and consequently rapidly loses its effectiveness when it is used in alkaline pH conditions and/or at temperatures higher than 40° C. In addition, these substances also have a sensitising effect on skin.

It is also possible to use substances containing bromine and, more generally, combinations of halogenated products. Such combinations are however undesirable in many cases since they can damage the environment, particularly in the field of danger of exposure to water. Due to their instability for a neutral and alkaline pH value, such biocides must in all cases be stabilised at an acid pH value and are used as such. In the case of a dosage made once and/or several times, problems of compatibility can occur with pigment solutions adjusted to a neutral and/or alkaline pH. The stability of such solutions can consequently be degraded in terms of their Brookfield™ viscosity. Very particularly for aqueous dispersions or suspensions with high concentrations of mineral matter, notably calcium carbonate and/or kaolin, it is possible to observe an increase of the viscosity and formation of agglomerates.

It is also known to use glutardialdehyde. Glutardialdehyde is unstable above temperatures of 40 to 45° C. and decomposes or forms ring-like structures, thus losing its efficacy. In addition, glutardialdehyde is currently the subject of many toxicological studies, relating notably to its carcinogenic character: it is, indeed, not certain that this product is devoid of all risks for humans in mutagenic terms. Although this aspect is not yet clearly demonstrated, conversely it is well known that glutardialdehyde can cause chronic respiratory illnesses and allergic complaints. Consequently, it represents a definite danger fix the users.

Another very large group of biocides lies in products which decompose giving formaldehyde. Generally speaking, these products are not very stable under heat and decompose spontaneously into formaldehyde at temperatures over 60° C. Formaldehyde is moreover suspected to be carcinogenic: according to a classification established by the European Union, it is placed in category no°3 as a "substance preoccupying for humans due to possible carcinogenic effects" and, due to its high volatility ($T_{eb}$=−19.2° C. for the pure product), it represents a major risk in the event of use. O-formals and N-formals, ethylene glycol bis hemiformal and benzyl-bishemiformal are mainly used as formaldehyde dissociators. According to the work entitled "Praxis der Sterilisation, Desinfektion-Konservierung, by Karl-Heinz Wallhausser, completely revised $5^{th}$ edition, published by Georg Thieme Verlag, Stuttgart, 1995, page 43", it is known that phenol derivates are used as anti-microbial active principles.

In document DE 100 27 588 A1, o-phenylphenol and its alkaline salts are proposed as preservation agents. The latter are indeed stable for an alkaline pH and active against most microorganisms but, due to their satisfactory chemical and thermal stability, it is however difficult to deactivate them. It is sometimes essential that their anti-bacterial effect should not be permanent: this is a requirement of the highest importance which is found notably in the paper manufacturing field. Thus, document WO 04/901.48 describes the enzymatic synthesis of a polymer of the acrylamide type, used as a coagulant and/or adhesive and/or thickening agent in the manufacture of paper. Furthermore, document CN 1 483 773 teaches the use of an enzymatic compound in a process to deink paper. One may also mention document JP 2004 169 243, which describes a process using an enzyme to whiten pulp used in the manufacture of paper. Consequently, these documents satisfactorily demonstrate the importance which certain enzymes may have in the paper manufacturing field: it is thus important to have a microbial protection measure the activity of which it is possible to control, in order not to harm the presence of the said enzymes, which are essential in certain paper manufacturing processes. In addition, it is known that o-phenylphenol has both a curative and a protective effect: both of these aspects are of equal importance for the skilled man in the art. A curative and protective effect is taken to mean respectively the characters of a process or a substance intended to ensure protection respectively against a subsequent infection or against an infection which has already occurred (as described in the document "Wörterbuch der Mikrobioiogie H. Weber, Gustav Fischer Verlag, Jena, Stuttgart, Lüber, Ulm", 1997, respectively on page 449 and page 321).

In addition, processes of dosing of microbial substances for disinfection and preservation of aqueous suspensions and/or dispersions have disadvantages in the areas of human protection, stability under heat and/or damage to the environment: their use must thus be avoided.

Another method to ensure the disinfection and preservation of water and/or of aqueous suspensions and/or of aqueous dispersions containing mineral matter lies in the use of treatment processes which do not involve chemicals.

In this respect, in the field of food products, firstly, substances with a microbicidal effect are sterilised and preserved, using notably heat (for example UHT process). Too high a heat can, however, lead to a modification of the products to be protected and cannot consequently be recommended in many cases. Vitamins, for example, can be destroyed by too high a temperature.

In the literature processes making use of electrophoresis are also described. In this case, hydrogen or oxygen in the nascent state is generated. However, it is well known that hydrogen in the nascent state, particularly in the presence of oxygen, poses a risk of explosion (explosive gas).

It is also known to accomplish sterilisation by means of X rays. Sources of X rays can however be dangerous if they are handled in a non-compliant manner; they require specially trained personnel and consequently have the disadvantage of being costly and difficult to put to use.

Furthermore, it is known that ozone is used as a disinfection agent. Ozone is however toxic and costly to manufacture and is consequently not especially suitable for use on site. Ozone can also degrade the effect of dispersing agents such as sodium polyacrylates which, again, leads to an undesirable increase of the viscosity of the aqueous suspension and/or dispersion to be treated.

UV radiation is also used, particularly UV-C radiation for sterilisation. UV radiation is however dangerous. UV light, for example, is used in sterilisation of water. Cloudy substances can however be poorly treated by the use of UV radiation (shadow phenomena).

"Hochschule CH-8820 Wädenswil", Switzerland, publishes a process which reduces bacteria by using strong electrical impulses ("High Electric Field Puls" process and ASE/AES bulletin 3/01, page 44): this also concerns a process which requires major modifications to the mineral matter manufacturing process for it to be used.

In addition, in the work "J. Food Prot. Vol. 64 No. 10 2001, pages 1579 to 1583, Author-Department of Applied Chemistry, Kanagawa Institute of Technology, Atsugi, Japan", a process for the disinfection of food products is described using charred crab shells. In this process shells are cooked at a temperature of over 850° C. and the CaO produced is proposed as a disinfectant agent for food products. The details of any negative effects on the processed products are not gone into. The skilled man in the art cannot, on the basis of this document, obtain any knowledge whatever concerning the influence produced on aqueous suspensions or dispersions of pigments obtained and on the modification of their properties, such as viscosity properties. In addition, nothing is said on the subject of an efficacy limited over time, and no reference is given to another possible treatment aimed at creating a time interval during which the system must act.

In addition, in Brock-Biology of Microorganisms—($9^{th}$ edition), Madigan, M. T., and Martinko, J. M., and Perker, J., 2000, Upper Saddle River, (Prentice-Hall, Inc.), pages 154 to 155 in FIG. 5.18 and in "Allgemeine Mikrobiologie, ($7^{th}$ edition), Schlegel, H. G., 1992, Georg Thieme Verlag, Stuttgart—New York, pages 194 to 196, it is mentioned that several microorganisms such as *bacillus* species can also live in an extremely alkaline environment. In this document, no mention is made of the fact that, by increasing or reducing the pH value, it is possible to obtain a temporary preservation of the aqueous suspensions of mineral matter without modifying the physical properties of the said suspensions in terms of viscosity. Moreover, this document, which would tend to demonstrate that certain microorganisms can subsist in alkaline pH conditions, does not encourage the skilled man in the art to put such alkaline pH conditions to use, precisely with a view to protecting and/or disinfecting aqueous suspensions of mineral matter, which is an object of the present invention. The Applicant is keen to stress that neither this process, nor the methods using heat, ozone, X or UV rays or electrical impulses, allow microbial growth to be controlled in the mineral matter suspensions to be treated. As it has been previously stated, this is an important requirement for the skilled man in the art, notably in the paper manufacturing industry.

Finally, document DE 19 811 742 describes a water treatment process to purify it with calcium carbonate and kaolin, by increasing the pH to a value of over 12, and preferentially over 12.6-12.8, through the addition of calcium oxide or hydroxide. This document, which is undoubtedly not in the special technical field of processes for treatment of aqueous suspensions of mineral matter to eliminate bacteria from them, cannot be passed over by the skilled man in the art: it refers to a more general process for treatment of such mineral matter suspensions, with a view to purifying them. It teaches that the addition of calcium oxide or hydroxide leads in this case to a flocculation of the suspended mineral matter, which is an unsought effect in connection with the technical problem which the Applicant is seeking to resolve (reduction or control of microbial growth). However, in a surprising manner, using the process developed in the present application, the problem posed is successfully resolved without however causing the suspended mineral matter to become flocculated, possibly through the addition of calcium oxide or hydroxide. Thus, in a surprising manner, the process according to the invention does not lead to a flocculation of the aqueous suspensions and dispersions of mineral matter to which it is applied.

Ultimately, use of biocides such as described in the prior art has many disadvantages, in terms of danger for humans and/or damage to the environment.

Secondly, the processes currently used to decontaminate aqueous suspensions of mineral matter generally prove costly, difficult to incorporate in a process to manufacture the said mineral matter, and also, hr their part, not free of dangers for the environment and risks for humans.

Furthermore, none of the habitual chemicals and none of the known processes of decontamination allow control of the development of growth, i.e. development of the cell division of the microbes and/or the total number of microbes over time, in the said aqueous suspensions of mineral matter. But, as the Applicant has previously indicated, this is a fundamental requirement for the skilled man in the art, notably in the paper manufacturing sector.

In addition, it is primordial to develop a process which does not modify the stability, in terms of the Brookfield™ viscosity, of the aqueous dispersions and/or suspensions of mineral matter thus obtained.

These problems are entirely resolved by the invention which consists in a process for disinfection and/or preservation and/or reduction and/or control of microbial contamination of aqueous dispersions and/or suspensions of mineral matter, characterised in that it uses:
   a) at least one stage to increase the $OH^-$ ion concentration of the said aqueous dispersions and/or suspensions, to a value greater than or equal to $1 \times 10^{-2}$ mole/l,
   b) at least one stage of dispersion and/or grinding of the said aqueous dispersions and/or suspensions, occurring before, during or after stage a), possibly using at least one dispersing agent and/or at least one grinding aid agent,
   c) possibly at least one stage to reduce the $OH^-$ ion concentration of the said aqueous dispersions and/or suspensions, occurring after stage a), to a value less than or equal to $1 \times 10^{-2}$ mole/l,
   d) possibly at least one stage of addition of at least one substance with a microbicidal effect and/or use of a physical decontamination process occurring before, during or after stage a) and/or b) and/or c).

The Applicant stresses that, once the process has thus been defined, stages a), b), c) and d) can be repeated as many times as required, as the skilled man in the art shall see fit; the latter shall know how to adapt the process according to the invention to the aqueous dispersions and/or suspensions of mineral matter which he envisages treating.

This process is thus characterised by an increase of the $OH^-$ ion concentration using one or more $OH^-$ ion donators, such as alkaline and/or alkaline earth oxides and/or alkaline and/or alkaline earth hydroxides, to reduce the speed of the biological cell division and/or cause the biological cell division to cease and/or to destroy the microbes present in the said aqueous dispersion and/or suspension.

And, as required, the $OH^-$ ion concentration of the aqueous suspension and/or dispersion is reduced, using one or more weak, moderately strong or strong, monovalent and/or polyvalent $H_3O+$ ion donators, such as, notably, gaseous $CO_2$ dissociated in carbonic acid water; this enables the natural growth of the microbial germs to be re-established.

This process allows, both in the phase to limit the growth of microbial germs, and in the phase of propagation of the said germs, all deterioration of the aqueous suspension and/or dispersion of mineral matter to be prevented with regard to its subsequent application, such as, for example, a deterioration of its suitability for storage, of its pumpability, and/or any modification of its rheological properties in terms of viscosity.

An important aim of the invention is thus to simplify the procedure of disinfection and/or preservation of the aqueous suspensions and/or dispersions of mineral matter in combination with other manufacturing stages, such as, notably, grinding and/or dispersion of the said mineral matter, without however modifying the stability in terms of the Brookfield™ viscosity of the said aqueous suspensions and/or dispersions of mineral matter.

Another aim of the invention is to provide an aqueous suspension and/or dispersion of mineral matter by a process allowing disinfection and/or protection of the said suspension and/or the said aqueous dispersion against all microbial contamination and/or microbial attacks, whilst doing minimal damage to humans, the environment or natural resources. In particular it is necessary to ensure that risky chemical substances are not used unnecessarily, bearing in mind that the combination of the process according to the invention, with the appropriate quantities used, of minimal harmfulness and/or lower quantities, of chemical substances, such as, for example, o-phenylphenol and its salts, may constitute a preferred embodiment. The process must be able to be applicable to aerobic and anaerobic species.

Another important aim of the invention is to control the development of growth, i.e. development of biological cell division and/or the total number of microorganisms over time, so as not to exceed a determined number of microbes. In addition, the microbicidal effect may be suppressed in a simple manner, without modifying the stability of the aqueous suspensions and/or dispersions treated in terms of Brookfield™ viscosity, without restricting their subsequent uses, notably in the paper manufacturing sector, through the use of enzymes, which is perfectly compatible with the process according to the invention.

Another aim of this invention concerns the purification and the disinfection of storage tanks, rail and road transport recipients, such as concrete and steel tanks, rail tanker wagons, tanks and containers. Rail tanker wagons which are used for transporting aqueous suspensions of pigments contain residual quantities of pigments in liquid form, which are partly concentrated by drying. On their return, they must be cleaned and disinfected to prevent all contamination of a new product to be loaded. The same applies for every storage and transport "recipient", whatever its size and volume. In this case, too, it is essential to cancel the "just in time" microbicidal effect in order not to expose humans, animals and the environment to any danger.

The problem is resolved according to the invention due to the fact that a process is provided which, alone or in combination with other processes, such as the additional use of appropriate substances with a microbicidal effect or a physical process, such as high voltage pulses, or thermal treatment, allows reduction and/or elimination and/or control of the growth of the microbial organisms, a process which has a limited action time and can be controlled. The process thus has as many curative effects as it has protective ones. Finally, the said process does not modify, or modifies only slightly, the stability, in terms of Brookfield™ viscosity of the said aqueous dispersions and/or suspensions of mineral matter thus treated.

The first object of the invention is thus a process for disinfection and/or preservation and/or reduction and/or control of microbial contamination of aqueous dispersions and/or suspensions of mineral matter, characterised in that it uses:
   a) at least one stage to increase the $OH^-$ ion concentration of the said aqueous dispersions and/or the said aqueous suspensions, to a value greater than or equal to $1 \times 10^{-2}$ mole/l,
   b) at least one stage of dispersion and/or grinding of the said aqueous dispersions and/or suspensions, occurring before, during or after stage a), possibly using at least one dispersing agent and/or at least one grinding aid agent,
   c) possibly at least one stage to reduce the $OH^-$ ion concentration of the said aqueous dispersions and/or suspensions, occurring after stage a), to a value less than or equal to $1 \times 10^{-2}$ mole/l,
   d) possibly at least one stage of addition of at least one substance with a microbicidal effect and/or use of a physical decontamination process occurring before, during or after stage a), and/or b), and/or c).

This process is characterised in that the $OH^-$ ion concentration value relative to stage a) is preferentially higher than or equal to $2 \times 10^{-2}$ mole/l.

This process is also characterised in that the $OH^-$ ion concentration increase, relative to stage a), is undertaken using one or more $OH^-$ ion donators, such as alkaline and/or alkaline earth oxides and/or alkaline and/or alkaline earth hydroxides.

This process is also characterised in that the $OH^-$ ion concentration value relative to stage c) is preferentially less than or equal to $1 \times 10^{-3}$ mole/l, and very preferentially less than or equal to $1 \times 10^{-4}$ mole/l.

This process is also characterised in that the $OH^-$ ion concentration reduction, relative to the possible stage c), is undertaken using one or more weak, moderately strong or strong, monovalent and/or polyvalent $H_3O^+$ ion donators, such as notably gaseous $CO_2$ dissociated in carbonic acid water.

This process is also characterised in that the possible stage d) of addition of at least one substance with a microbicidal effect and/or use of a physical process of microbicidal decontamination uses at least one biocide and notably o-phenylphenol and/or its salts or indeed their mixtures, and/or at least one product containing a germ which destroys microbial germs, preferably pseudomonas germs, and more preferably *pseudomonas aeruginosa* germs, and in that the destructive germ is of the Bdellovibrio family, and is very preferentially the Bdellovibrio bacteriovorus germ.

This process is also characterised in that the possible stage d) of addition of at least one substance with a microbicidal effect and/or use of a physical process of microbicidal decontamination uses at least one physical process, such as preferentially processes based on an increase of temperature.

In an embodiment of this process corresponding to the accomplishment of stage c), the said process is characterised in that stage c) occurs preferentially between one week and one month after stage a).

According to this embodiment, no substance with a microbicidal effect is then used in the aqueous dispersions and/or suspensions of mineral matter to be treated.

This process is also characterised in that it may be used discontinuously, semi-continuously or continuously, according to the terminology with which the skilled man in the art is very familiar.

This process is also characterised in that it has curative and/or protective effects with regard to the waters and/or aqueous dispersions and/or suspensions of mineral matter to be treated.

This process is also characterised in that the minerals and/or pigments and/or fillers which it uses are chosen from among kaolin, aluminium hydroxide, titanium dioxide, talc, gypsum, satin white, mica, minerals and/or fillers and/or pigments containing calcium carbonate, and in particular natural calcium carbonates, marble, limestone, dolomite or their mixtures, their mixtures with other minerals, such as talc-calcium carbonate mixtures, calcium carbonate-kaolin mixtures, or again mixtures of calcium carbonate with aluminium trihydroxide or aluminium trioxide, or again mixtures with synthetic or natural fibres, or again co-structures of minerals such as talc-calcium carbonate or talc-titanium dioxide co-structures, or their mixtures, and/or calcium carbonates containing dolomite, together with calcium carbonates manufactured in a synthetic manner by precipitation and/or calcium carbonate precipitates with other minerals. Preferentially, these minerals and/or pigments and/or fillers are chosen from among natural and/or precipitated calcium carbonate, and very preferentially are chosen from among natural calcium carbonates and notably from among marble, calcite, chalk and their mixtures.

Finally, this process is characterised in that it is used in mineral industry fields, and notably in storage tanks, rail and road transport recipients, such as concrete and steel tanks, rail tanker wagons, tanks and containers, in the paper industry, preferably in paper manufacturing, and/or in coating colours, and in the field of the manufacture of water-based paints and also in lacquers and varnishes.

Another object of the invention lies in aqueous dispersions and/or suspensions of mineral matter obtained by use of the process according to the invention.

These dispersions and/or suspensions are also characterised in that they contain a mineral and/or pigment and/or filler chosen from among kaolin, aluminium hydroxide, titanium dioxide, talc, gypsum, satin white, mica, minerals and/or fillers and/or pigments containing calcium carbonate, and in particular natural calcium carbonates, marble, limestone, dolomite or their mixtures, their mixtures with other minerals, such as talc-calcium carbonate mixtures, calcium carbonate-kaolin mixtures, or again mixtures of calcium carbonate with aluminium trihydroxide or aluminium trioxide, or again mixtures with synthetic or natural fibres, or again co-structures of minerals such as talc-calcium carbonate or talc-titanium dioxide co-structures, or their mixtures, and/or calcium carbonates containing dolomite, together with calcium carbonates manufactured in a synthetic manner by precipitation and/or calcium carbonate precipitates with other minerals. Preferentially, these minerals and/or pigments and/or fillers are chosen from among natural and/or precipitated calcium carbonate, and very preferentially are chosen from among natural calcium carbonates and notably from among marble, calcite, chalk and their mixtures.

In a first embodiment in which stage c) of the process according to the invention is not used, these said dispersions and/or suspensions are characterised:
a) in that they have a OH⁻ ion concentration higher than or equal to $1 \times 10^{-2}$ mole/l, and preferentially higher than or equal to $2 \times 10^2$ mole/l,
b) in that they have a microbe concentration lower than or equal to 100 microbes/gram, and preferentially less than or equal to 10 microbes/gram,
c) and in that they contain:
1. mineral matter,
2. water,
3. possibly at least one dispersing agent and/or at least one grinding aid agent,
4. possibly at least one anti-foaming agent,
5. possibly at least one microbicidal agent.

According to this embodiment, these dispersions and/or suspensions are also characterised in that they contain:
1. 0.1% to 85% by dry weight of mineral matter,
2. 15% to 99.9% by weight of water,
3. 0% to 5% by dry weight of at least one dispersing agent and/or at least one grinding aid agent,
4. 0% to 5% by dry weight of at least one anti-foaming agent,
5. 0 to 5% by dry weight of at least one microbicidal agent,
relative to the total weight of the said dispersions and/or suspensions.

These aqueous dispersions and/or suspensions are also characterised in that the substance with microbicidal effect is chosen from among o-phenylphenol, it salts or again their mixtures, and/or at least one product containing a germ which destroys microbial germs, preferably pseudomonas germs, and more preferably *pseudomonas aeruginosa* germs, and in that the destructive germ is from the Bdellovibrio family, and is very preferentially the Bdellovibrio bacteriovorus germ.

Still according to this embodiment, and when, according to stage d) a process based on the increase of temperature is used, these aqueous dispersions and/or suspensions are also characterised in that the microbial concentration is less than 10 microbes/gram.

In a second embodiment, in which stage c) of the process according to the invention is used, and in which no substance with a microbicidal effect is used according to stage d), these said aqueous dispersions and/or suspensions are characterised:
a) in that they have a OH⁻ ion concentration lower than or equal to $1 \times 10^{-2}$ mole/l, and preferentially lower than or equal to $1 \times 10^{-3}$ mole/l, and very preferentially lower than or equal to $1 \times 10^{-4}$ mole/l,
b) in that they have a microbe concentration lower than or equal to 100 microbes/gram, and preferentially less than or equal to 10 microbes/gram,
c) and in that they contain:
1. mineral matter,
2. water,
3. at least one dispersing agent and/or at least one grinding aid agent,
4. and possibly at least one anti-foaming agent, According to this embodiment, these dispersions and/or suspensions according to the invention are also characterised in that they contain:
1. 0.1% to 85% by dry weight of mineral matter,
2. 10% to 99.89% by weight of water,
3. 0.01% to 5% by dry weight of at least one dispersing agent and/or at least one grinding aid agent,
4. 0% to 5% by dry weight of at least one anti-foaming agent,
relative to the total weight of the said dispersions and/or suspensions.

According to this embodiment, the anti-foaming agent is notably chosen from among siloxane compounds, fatty acid esters and their mixtures.

Still according to this embodiment, and when, according to stage d) a process based on the increase of temperature is used, these aqueous dispersions and/or suspensions are also characterised in that the microbial concentration is less than or equal to 10 microbes/gram.

Another purpose of the invention consists in the use of the said aqueous suspensions and/or dispersions of mineral matter in the mineral industry, in the paper industry, preferably in the manufacture of paper, and/or in paper coating, and also in the field of manufacture of water-based paints, and also in lacquers and varnishes.

A final purpose of the invention lies in mineral formulations, paper formulations and notably paper sheets and coating colours, water-based paints, lacquers and varnishes characterised in that they contain the said suspensions and/or dispersions according to the invention.

The present invention is described in greater detail below using examples of embodiments and comparative examples. The invention is not however limited to the following examples. The skilled man in the art is able, without using any inventive activity, using the present description, jointly with the claims, to formulate other examples and to find other fields of application.

EXAMPLES

General Observations Concerning the Manner of Proceeding

The habitual methods for determining germs in the food products industry and in the paper and pigments industry are, for example, described in the Swiss manual on food products, section 56, paragraph 7.01, edition 1985, revision 1988, entitled "Bestimmung von aeroben Bakterien und Keime" and in the Swiss food products manual, section 56, paragraph 7.22, edition 1985, revision 1988, entitled "Bestimmung von Pilzen" Habitually, the incubation time before being able to undertake the determination is each time approximately 48 hours. An incubation time of 5 days is applied in order to detect the presence of spores.

The company Microbial Systems Ltd has developed the device and the process for analysing particles sold under the name Cellfacts™ R. Additional information on the subject is found in the journal entitled Labor flash 9/96, offering a reader service for the laboratory and research, Ott Verlag+ Druck AG, Ch-3607 Thun, Switzerland.

These devices enable the bacteria concentration in a sample to be determined, possibly by extrapolation, as particles present in an electric field. The device in question together with the measurement method and the corresponding calculations are described in detail in European patent EP 1 149 1 72.

The suspensions of pigments used in the examples were produced by grinding and/or dispersion in the presence of sodium polyacrylates. The mass of the initial sample was 5 kg. A ball mill of the Dynomill type, of capacity equal to 2 litres, with a stirrer having a toothed disk of diameter 50 mm, was used. As a grinding body glass beads of diameter 2 mm and zircon silicate beads of diameter 0.5 to 2 mm were used, but also other types of grinding balls such as, notably, porcelain, zirconium silicate, zirconium oxides such as baddeleyite, and their mixtures and/or aluminium oxides or autogenous grinding agents.

The aqueous suspensions and/or dispersions of mineral matter were sterilised for one hour at 141° C. in autoclaves for an examination of the protective effects of the process according to the invention.

The suspensions and/or dispersions were incubated for one week at 32° C. in an incubation oven, then mixed again with the corresponding quantity and type of tested is bacteria, for an examination of the curative effects of the process according to the invention.

At certain time intervals, the germs were quantified according to the method "Bestimmung von aeroben mesophilen Keimen", Schweizerisches Lebensmittelbuch, section 56, paragraph 7.01, edition 1985, revision 1988.

The OH⁻ ion molar concentration values were always determined at a temperature of 22° C. (the constant of dissociation of water, pKw, was then equal to 14)

$$K = \frac{[C_{H3O+}] \times [C_{OH-}]}{[C_{H2O}]^2}$$

For water at 22° C., in which $C_{H3O+} = C_{OH-} = 10^{-7}$ M, we have: $K_{water}$ (Kw) (22° C.)=$10^{-14}$ M².

The constant of dissociation of water, $pK_w$, is a function of the temperature. Thus, a pH value 10 measured at 22° C. corresponds to a OH⁻ ion concentration which would lead to a pH value equal to 11 if it were measured at 100° C.

Consequently, in order to take account of the influence of temperature, the following table was used to determine the values of the constant of dissociation of water:

| Temperature[° C.] | $K_w$ [M²] | $pK_w = -\log_{10} K_w$ |
|---|---|---|
| 0 | 0.13 × 10⁻¹⁴ | 14.89 |
| 10 | 0.36 × 10⁻¹⁴ | 14.45 |
| 16 | 0.63 × 10⁻¹⁴ | 14.20 |
| 20 | 0.86 × 10⁻¹⁴ | 14.07 |
| 22 | 1.00 × 10⁻¹⁴ | 14.00 |
| 30 | 1.89 × 10⁻¹⁴ | 13.73 |
| 50 | 5.60 × 10⁻¹⁴ | 13.25 |
| 100 | 74.00 × 10⁻¹⁴ | 12.13 |

Furthermore, in all the remainder of the present application, it is indicated that the expression Brookfield™ viscosity refers to the Brookfield™ viscosity measured on a viscometer of the same name and of type RVT, at a speed of 100 RPM, using module no 3,

Example 1

The aim of this example is to illustrate the process according to the invention, in its curative mode, applied to an aqueous suspension of mineral matter which is calcium carbonate.

Its aim is also to illustrate that the process according to the invention allows the development of the growth of microbial germs to be controlled in such a suspension, without modifying its stability significantly.

Pigment Suspension:

An aqueous suspension of 78.3% by weight of natural marble (of which 90% by weight of the particles have a diameter of less than 2 μm, and 65 by weight of the particles have a diameter of less than 1 μm), obtained by grinding, was prepared, using 0.65% by dry weight of a polyacrylate neutralised by a commercially available sodium/magnesium mixture, relative to the dry weight of mineral matter.

The pH value of the suspension after grinding was 9.7 measured at 20° C.

Each time 2 samples of one kilogram of the pigment suspension were prepared.

Microbial Suspension

A mixture of 7 different types of microbes was produced, gram-negatives, mainly produced from the family of pseudomonas (the majority being *pseudomonas aeruginosa*), isolated from a suspension of calcium carbonate having germinated naturally, originating from Austria.

The 7 different varieties of microbes were able to be identified using the API™ test which is well known to the skilled man in the art, and developed by the company BIOMERIEUX™.

In this suspension, the microbial germ concentration is $5 \times 10^6$ germs/ml.

Sample 1

The $1^{st}$ sample corresponds to 1 kg of the said pigment suspension, which was mixed with 0.025 mole of $OH^-$ ions through the addition of sodium hydroxide, with substantial stirring. (NaOH was added as a 2.5 molar solution).

The Brookfield™ viscosity immediately after the addition of sodium hydroxide was 308 mPa·s.

Sample 2

The $2^{nd}$ sample was used as a comparative sample relative to the state of the technique, and corresponds to 1 kg of the pigment suspension described at the start of example 1, without addition of the $OH^-$ ion donator solution.

The Brookfield™ viscosity was 389 mPa·s.

Both samples were then mixed with 10 ml of microbial suspension and then incubated each time for 24 hours at 30° C. in an incubation oven: in the remainder of the application, this action is designated under the term exposure. For each example, the samples are exposed to the same bacterial suspension.

For each sample the germ concentration (in number/ml), the $OH^-$ ion concentration values (in mole/l), and the Brookfield™ viscosity (mPa·s) were then measured.

This data is shown in tables 1 and 2.

TABLE 1

|  | $OH^-$ concentration (mole/l) | | Germ concentration (number/ml) | |
| --- | --- | --- | --- | --- |
|  | Sample 1 | Sample 2 | Sample 1 | Sample 2 |
| Immediately before the $1^{st}$ exposure | $1.6 \times 10^{-2}$ | $5 \times 10^{-5}$ | $<10^2$ | $<10^2$ |
| Immediately after the $1^{st}$ exposure | $1.6 \times 10^{-2}$ | $5 \times 10^{-5}$ | $<10^2$ | $1 \times 10^5$ |
| Measure 3 days after the $1^{st}$ exposure, then $2^{nd}$ exposure | $1.6 \times 10^{-2}$ | $5 \times 10^{-5}$ | $<10^2$ | $1 \times 10^5$ |
| 4 days after the $2^{nd}$ exposure | $1.6 \times 10^{-2}$ | $5 \times 10^{-5}$ | $<10^2$ | $4 \times 10^7$ |

These results demonstrate the protective effect of the treatment according to the invention on sample 1: there was no increase in the number of microbes.

TABLE 2

|  | $OH^-$ concentration (mole/l) | | Brookfield™ viscosity (mPa·s) | |
| --- | --- | --- | --- | --- |
|  | Sample 1 | Sample 2 | Sample 1 | Sample 2 |
| Immediately before the $1^{st}$ exposure | $1.6 \times 10^{-2}$ | $5 \times 10^{-5}$ | 310 | 390 |
| 1 day after the $1^{st}$ exposure | $1.6 \times 10^{-2}$ | $5 \times 10^{-5}$ | 518 | 463 |
| 5 days after the $1^{st}$ exposure: $2^{nd}$ exposure | $1.6 \times 10^{-2}$ | $5 \times 10^{-5}$ | 804 | 676 |
| 4 days after the $2^{nd}$ exposure | $1.6 \times 10^{-2}$ | $5 \times 10^{-5}$ | 661 | 560 |
| 26 days after the $1^{st}$ exposure: | $1.6 \times 10^{-2}$ | $5 \times 10^{-5}$ | 907 | 790 |

TABLE 2-continued

|  | $OH^-$ concentration (mole/l) | | Brookfield™ viscosity (mPa·s) | |
| --- | --- | --- | --- | --- |
|  | Sample 1 | Sample 2 | Sample 1 | Sample 2 |
| 26 days after the $1^{st}$ exposure and after 5 minutes of intense stirring | $1.6 \times 10^{-2}$ | $5 \times 10^{-5}$ | 339 | 430 |

In addition, the Brookfield™ viscosity of the sample according to the invention is not modified: it changes in a manner similar to that of the untreated sample.

Finally, the Brookfield™ viscosities at 26 days, measured after stifling, are very close to the initial Brookfield™ viscosities: the treatment according to the invention does not therefore modify the stability of the aqueous suspensions of mineral matter in terms of the Brookfield™ viscosity.

After 26 days, a part of sample 1 according to the invention having been subject to the previous exposures was treated through the introduction of gaseous $CO_2$, so as to reduce the $OH^-$ ion concentration to a value equal to $5 \times 10^{-5}$ mole/l.

This instant corresponds to the instant T=0 for this new sample.

This part of sample 1, henceforth called sample 1-2, and representing the invention, will be subjected to a certain number of additional exposures.

For sample 1-2 measurements of the $OH^-$ ion concentration, of the number of microbial germs, and of the Brookfield™ viscosity will then be taken.

The results are shown in tables 3 and 4.

TABLE 3

| (sample 1-2) | | |
| --- | --- | --- |
|  | $OH^-$ concentration (mole/l) | Germ concentration (number/ml) |
| Immediately before the $1^{st}$ exposure | $5 \times 10^{-5}$ | $<10^2$ |
| Immediately after the $1^{st}$ exposure | $6 \times 10^{-5}$ | $2 \times 10^6$ |

TABLE 4

| (sample 1-2) | | |
| --- | --- | --- |
|  | $OH^-$ concentration (mole/l) | Brookfield™ viscosity (mPa·s) |
| Immediately before the $1^{st}$ exposure | $5 \times 10^{-5}$ | 238 |
| 1 day after the $1^{st}$ exposure | $6 \times 10^{-5}$ | 580 |
| 5 days after the $1^{st}$ exposure: $2^{nd}$ exposure | $1 \times 10^{-4}$ | 790 |
| 12 days after the $1^{st}$ exposure | $8 \times 10^{-5}$ | 648 |
| 26 days after the $1^{st}$ exposure | $8 \times 10^{-5}$ | 998 |
| 26 days after the $1^{st}$ exposure and after 5 minutes of intense stirring | $1 \times 10^{-5}$ | 358 |

The Brookfield™ viscosity without stirring of sample 1-2 according to the invention only increases slightly over the duration of the storage relative to the comparative sample. The stability is not degraded. The Brookfield™ viscosity in the stirred state after 26 days is almost identical to the initial Brookfield™ viscosity before the treatment according to the invention: the stability of the sample according to the invention is not thus modified in terms of the Brookfield™ viscosity.

After 26 days, another part of sample 1 according to the invention having been subjected to the previous exposures as described at the start of this example was treated through the introduction of nitric acid, so as to reduce the OH⁻ ion concentration to a value equal to $8 \times 10^{-5}$ mole/l.

This instant corresponds to the instant T=0 for this new sample.

This part of sample 1, henceforth called sample 1-3, and representing the invention, will be subjected to a new exposure.

For sample 1-3 the measurements of the OH⁻ ion concentration and of the number of microbial germs will then be taken.

The results are shown in table 5.

TABLE 5

(sample 1-3)

|  | OH⁻ concentration (mole/l) | Germ concentration (number/ml) |
|---|---|---|
| Immediately before the 1$^{st}$ exposure | $8 \times 10^{-5}$ | $<10^2$ |
| Immediately after the 1$^{st}$ exposure | $1 \times 10^{-4}$ | $2 \times 10^5$ |

The inhibitory effect was again eliminated through the addition of $H_3O^+$ ions by means of the addition of citric acid, i.e. by means of the process according to the invention.

After 26 days, another part of sample 1 according to the invention having been subjected to the previous exposures as described at the start of this example was treated through the introduction of phosphoric acid, so as to reduce the OH⁻ ion concentration to a value equal to $2.5 \times 10^{-5}$ mole/l.

This instant corresponds to the instant T=0 for this new sample.

This part of sample 1, henceforth called sample 1-4, and representing the invention, will be subjected to a new exposure.

For sample 1-4 the measurements of the OH⁻ ion concentration and of the number of microbial germs will then be taken.

The results are shown in table 6,

TABLE 6

(sample 1-4)

|  | OH⁻ concentration (mole/l) | Germ concentration (number/ml) |
|---|---|---|
| Immediately before the 1$^{st}$ exposure | $2.5 \times 10^{-5}$ | $<10^2$ |
| Exposure | $2.5 \times 10^{-5}$ | $>10^6$ |

The inhibitory effect was again eliminated through the addition of $H_3O^+$ ions through the addition of citric acid, i.e. by means of the process according to the invention.

Example 2

The aim of this example is to illustrate the process according to the invention, in its curative and protective mode, applied to an aqueous suspension of mineral matter which is calcium carbonate.

Its aim is also to illustrate that the process according to the invention allows the development of the growth of microbial germs to be controlled in such a suspension, without modifying its stability in terms of Brookfield™ viscosity.

Pigment Suspension

An aqueous suspension of 78.3% by weight of natural marble (of which 90% by weight of the particles have a diameter of less than 2 μm, and 65% by weight of the particles have a diameter of less than 1 μm), obtained by grinding, was prepared, using 0.65% by dry weight relative to the dry weight of mineral matter, of a polyacrylate neutralised by a commercially available sodium/magnesium mixture. The pH value of the suspension after grinding was 9.7 measured at 20° C.

2 samples of 1 kg were prepared from the pigment suspension.

Microbial Suspension

A mixture of 7 types of different gram-negative bacteria was prepared, mostly comprised according to the family of pseudomonads (for the most part *pseudomonas aeruginosa*), isolated from a calcium carbonate slurry seeded naturally with germs, originating from Austria.

The 7 different varieties of microbes were able to be identified using the API™ test which is well known to the skilled man in the art, and developed by the company BIOMERIEUX™.

The microbial germ concentration of this suspension is $5 \times 10^6$ germs/ml.

Sample 3

This sample is used to illustrate the treatment according to the invention, in its protective mode.

This sample corresponds to 1 kg of the said pigment suspension, which was mixed under substantial stirring, in a solution of ground $Ca(OH)_2$ (with the average diameter of the particles being equal to 2 μm) containing $2.6 \times 10^{-2}$ mole/l of OH⁻ ions.

The Brookfield™ viscosity immediately after the previous addition was 357 mPa·s.

This sample according to the invention was then mixed several times with 10 ml of microbial suspension, and then incubated in an incubation oven, for 24 hours at 30° C.

Sample 3 was subjected to a number of exposures, and the OH⁻ ion concentration, germ concentration (number/gram) and Brookfield™ viscosity (mPa·s) values were then also measured.

The corresponding results are shown in tables 7 and 8.

TABLE 7

(sample 3)

|  | OH⁻ concentration (mole/l) | Germ concentration (number/ml) |
|---|---|---|
| Immediately before the 1$^{st}$ exposure | $2 \times 10^{-2}$ | $<10^2$ |
| Immediately after the 1$^{st}$ exposure | $2 \times 10^{-2}$ | $<10^2$ |
| 3 days after the 1$^{st}$ exposure: 2$^{nd}$ exposure | $2 \times 10^{-2}$ | $<10^2$ |
| 4 days after the 2$^{nd}$ exposure | $2 \times 10^{-2}$ | $<10^2$ |

These results demonstrate the protective effect of the treatment according to the invention on sample 3: there was no increase in the number of microbial germs.

TABLE 8

(sample 3)

| | OH⁻ concentration (mole/l) | Brookfield™ viscosity (mPa·s) |
|---|---|---|
| Immediately before the 1$^{st}$ exposure | $2 \times 10^{-2}$ | 357 |
| 1 day after the 1$^{st}$ exposure | $2 \times 10^{-2}$ | 909 |
| 5 days after the 1$^{st}$ exposure: 2$^{nd}$ exposure | $2 \times 10^{-2}$ | 888 |
| 4 days after the 2$^{nd}$ exposure | $2 \times 10^{-2}$ | 747 |
| 26 days after the 1$^{st}$ exposure | $2 \times 10^{-2}$ | 999 |
| 26 days after the 1$^{st}$ exposure and after 5 minutes of intense stirring | $2 \times 10^{-2}$ | 420 |

In addition, the Brookfield™ viscosity of the sample according to the invention is not modified: it changes in a manner similar to that of the untreated sample, represented by sample 2.

Finally, the Brookfield™ viscosities at 26 days, measured after stirring, are very close to the initial Brookfield™ viscosities: the treatment according to the invention thus enables the Brookfield™ viscosity to be regained.

After 26 days, a part of sample 3 according to the invention having been subject to the previous exposures was treated through the introduction of gaseous CO$_2$, so as to reduce the OH⁻ ion concentration to a value equal to $5 \times 10^{-5}$ mole/l.

This instant corresponds to the instant T=0 for this new sample.

This part of sample 3, henceforth called sample 3-2, and representing the invention, will be subjected to a certain number of exposures.

For sample 3-2, measurements of the OH⁻ ion concentration (mol/l), of the number of microbial germs (number/gram), and of the Brookfield™ viscosity (mPa·s) will then be taken.

The corresponding results are shown in tables 9 and 10.

TABLE 9

(sample 3-2)

| | OH⁻ concentration (mole/l) | Germ concentration (number/ml) |
|---|---|---|
| Immediately before the 1$^{st}$ exposure | $5 \times 10^{-5}$ | $<10^2$ |
| Immediately after the 1$^{st}$ exposure | $6 \times 10^{-5}$ | $2 \times 10^6$ |

These results demonstrate that after reduction of the OH⁻ ion concentration according to the invention, growth of microbial germs is restarted: the process according to the invention thus enables the growth of microbial germs in aqueous suspension of mineral matter to be controlled.

TABLE 10

(sample 3-2)

| | OH⁻ concentration (mole/l) | Brookfield™ viscosity (mPa·s) |
|---|---|---|
| Immediately before the 1$^{st}$ exposure | $5 \times 10^{-5}$ | 212 |
| 1 day after the 1$^{st}$ exposure | $5 \times 10^{-5}$ | 351 |
| 5 days after the 1$^{st}$ exposure: 2$^{nd}$ exposure | $6 \times 10^{-5}$ | 474 |
| 12 days after the 1$^{st}$ exposure | $8 \times 10^{-5}$ | 332 |

TABLE 10-continued (sample 3-2)

| | OH⁻ concentration (mole/l) | Brookfield™ viscosity (mPa·s) |
|---|---|---|
| 26 days after the 1$^{st}$ exposure | $8 \times 10^{-5}$ | 622 |
| 26 days after the 1$^{st}$ exposure and after 5 minutes of intense stirring | $6 \times 10^{-5}$ | 229 |

In addition, the Brookfield™ viscosity of the sample according to the invention is not modified: it changes in a manner similar to that of the untreated sample, represented by sample 2.

Finally, the Brookfield™ viscosities at 26 days, measured after stirring, are very close to the initial Brookfield™ viscosities: the treatment according to the invention thus enables the Brookfield™ viscosity to be regained.

Sample 4

This sample is used to illustrate treatment according to the invention, in its curative mode.

This sample according to the invention corresponds to 1 kg of the pigment suspension described at the start of this example, and which was mixed under substantial stirring with 10 ml of microbial suspension, and then incubated in an incubation oven, for 7 days at 32° C. The microbial concentration after one week's incubation was $2 \times 10^7$ germs/ml.

This sample was mixed under substantial stirring, in a solution of ground Ca(OH)$_2$ (with the average diameter of the particles being equal to 2 μm) containing $2.6 \times 10^{-2}$ mole/l of OH⁻ ions.

The Brookfield™ viscosity immediately after the previous addition was 389 mPa·s.

Sample 4 was subjected to a new exposure, and the OH⁻ ion concentration (mol/l), germ concentration (number/gram) and Brookfield™ viscosity (mPa·s) values were then also measured.

These results are shown in tables 11 and 12.

TABLE 11

(sample 4)

| | OH⁻ concentration (mole/l) | Germ concentration (number/ml) |
|---|---|---|
| 1 day after exposure | $2 \times 10^{-2}$ | $<10^2$ |
| 2 days after exposure | $2 \times 10^{-2}$ | $<10^2$ |
| 7 days after exposure | $2 \times 10^{-2}$ | $<10^2$ |

These results demonstrate the curative effect of the treatment according to the invention.

TABLE 12

(sample 4)

| | OH⁻ concentration (mole/l) | Brookfield™ viscosity (mPa·s) |
|---|---|---|
| 1 day after exposure | $2 \times 10^{-2}$ | 320 |
| 2 days after exposure | $2 \times 10^{-2}$ | 410 |
| 7 days after exposure | $2 \times 10^{-2}$ | 440 |

In addition, the Brookfield™ viscosities are not degraded.

After 7 days, a part of sample 4 according to the invention having been subject to the previous exposures was treated through the introduction of gaseous $CO_2$, so as to reduce the $OH^-$ ion concentration to a value equal to $3 \times 10^{-5}$ mole/l. This part of sample 4, named 4-2, was then re-exposed to 1 ml of microbial suspension.

This instant corresponds to the instant T=0 for this new sample.

For sample 4-2, measurements of the $OH^-$ ion concentration (mol/l), of the microbial germs concentration (number/gram), and of the Brookfield™ viscosity (mPa·s) were then taken.

These results are shown in tables 13 and 14.

TABLE 13

(sample 4-2)

| | $OH^-$ concentration (mole/l) | Germ concentration (number/ml) |
|---|---|---|
| 1 day after exposure | $4 \times 10^{-5}$ | $<10^2$ |
| 2 days after exposure | $4 \times 10^{-5}$ | $<10^2$ |
| 7 days after exposure | $3 \times 10^{-5}$ | $2 \times 10^6$ |

These results demonstrate that the process according to the invention enabled the microbial germ concentration to be increased anew: the process according to the invention thus enables the microbial concentration in the sample to be controlled.

TABLE 14

(sample 4-2)

| | $OH^-$ concentration (mole/l) | Brookfield viscosity (mPa·s) |
|---|---|---|
| 1 day after exposure | $4 \times 10^{-5}$ | 360 |
| 2 days after exposure | $4 \times 10^{-5}$ | 330 |
| 7 days after exposure | $3 \times 10^{-5}$ | 470 |

In addition, the Brookfield™ viscosities are not degraded by using the process according to the invention.

A part of sample 4, named sample 4-3, and resulting from the first curative preservation, was reduced to an $OH^-$ ion concentration value equal to $3 \times 10^{-5}$ mole/l through the addition of liquid $CO_2$.

This sample was mixed under substantial stirring, in a solution of ground $Ca(OH)_2$ (with the average diameter of the particles being equal to 2 μm) containing $2.6 \times 10^{-2}$ mole/l of $OH^-$ ions.

This moment was chosen as the new time origin.

The Brookfield™ viscosity immediately after the previous addition was now 425 mPa·s. The value of the $OH^-$ ion concentration measured at 20° C. was $6.3 \times 10^{-3}$ mole/l.

For sample 4-3, measurements of the $OH^-$ ion concentration (mol/l), of the microbial germs concentration (number/gram), and of the Brookfield™ viscosity (mPa·s) were then determined.

These results are shown in tables 15 and 16.

TABLE 15

(sample 4-3)

| | $OH^-$ concentration (mole/l) | Germ concentration (number/ml) |
|---|---|---|
| 1 day after exposure | $6.3 \times 10^{-3}$ | $<10^2$ |
| 2 days after exposure | $6.3 \times 10^{-3}$ | $<10^2$ |
| 7 days after exposure | $6.3 \times 10^{-3}$ | $<10^2$ |

TABLE 16

(sample 4-3)

| | $OH^-$ concentration (mole/l) | Brookfield™ viscosity (mPa·s) |
|---|---|---|
| 1 day after exposure | $6.3 \times 10^{-3}$ | 410 |
| 2 days after exposure | $6.3 \times 10^{-3}$ | 440 |

These results demonstrate that the process according to the invention enabled microbial growth to be stopped by a new increase in the $OH^-$ ion concentration: the process according to the invention thus enables the microbial contamination in the sample to be controlled.

In addition, the Brookfield™ viscosities are not degraded.

After 7 days, a part of sample 4-3 according to the invention was treated through the introduction of gaseous $CO_2$, so as to reduce the $OH^-$ ion concentration to a value equal to $3 \times 10^{-5}$ mole/l. This part of sample 4, named 4-4, was then re-exposed to 1 ml of microbial suspension.

This instant corresponds to the instant T=0 for this new sample.

For sample 4-4, measurements of the $OH^-$ ion concentration (mol/l), of the microbial germs concentration (number/gram), and of the Brookfield™ viscosity (mPa·s) were then taken.

TABLE 17

(sample 4-4)

| | $OH^-$ concentration (mole/l) | Germ concentration (number/ml) |
|---|---|---|
| 1 day after exposure | $2.5 \times 10^{-5}$ | $<10^2$ |
| 2 days after exposure | $2.5 \times 10^{-5}$ | $2 \times 10^6$ |

These results demonstrate that the process according to the invention enabled the microbial germ concentration to be increased anew: the process according to the invention thus enables the microbial concentration in the sample to be controlled.

TABLE 18

(sample 4-4)

| | $OH^-$ concentration (mole/l) | Brookfield™ viscosity (mPa·s) |
|---|---|---|
| 1 day after exposure | $2.5 \times 10^{-5}$ | 560 |
| 2 days after exposure | $2.5 \times 10^{-5}$ | 530 |
| 7 days after exposure | $2.5 \times 10^{-5}$ | 570 |

In addition, the Brookfield™ viscosities are not degraded by using the process according to the invention.

Example 3

The aim of this example is to illustrate the process according to the invention, in its curative mode, applied to an aqueous suspension of mineral matter which is kaolin.

Its aim is also to illustrate that the process according to the invention allows the development of the growth of microbial germs to be controlled in such a suspension.

Pigment Suspension

An aqueous suspension was manufactured containing 63.3% by dry weight of American kaolin (Georgia) (of which 95% by weight of the particles have a diameter of less than 2 µm, and 70% by weight of the particles have a diameter of less than 1 µm), by grinding to a concentration of 25% by weight, followed by drying in a pulverisation drying machine, and dispersion in water with use of 0.25% by dry weight relative to the dry weight of mineral matter of commercially available sodium polyacrylate.

The pH value of the suspension after grinding was 7.7 measured at 20° C.

2 samples of 1 kg were prepared from the pigment suspension.

Microbial Suspension

A mixture of 7 different types of bacteria was produced, which were gram-negatives, mainly formed from the family of pseudomonads the majority being *Pseudomonas aeruginosa*), isolated from a suspension of calcium carbonate having germinated naturally, originating from Austria.

The 7 different varieties of microbes were able to be identified using the API™ test which is well known to the skilled man in the art, and developed by the company BIOMERIEUX™.

The microbe concentration is $5 \times 10^6$ germs/ml.

Sample 5

Sample 5 corresponding to 1 kg of the said pigment suspension was mixed under substantial stilling in 0.053 mole of $OH^-$ ions (added in the form of a CaO solution in ethylene glycol at a concentration of 2.7 M).

The Brookfield™ viscosity of the aqueous suspension of kaolin immediately after addition of the CaO was 327 mPa·s.

The value of the $OH^-$ ion concentration was $1.25 \times 10^{-2}$ mole/l.

Sample 6

Sample 6 illustrates the prior art and corresponds to the mixture of the pigment suspension and the microbial suspension.

By using the previous notations, samples 6 and 7 were subjected to a number of exposures, and the $OH^-$ ion concentration (mold), microbial germ concentration (number/gram) and Brookfield™ viscosity (mPa·s) values were then measured.

These results are shown in tables 19 and 20.

TABLE 19

(samples 5 and 6)

|  | $OH^-$ concentration (mole/l) | | Germ concentration (number/ml) | |
| --- | --- | --- | --- | --- |
|  | Sample 5 | Sample 6 | Sample 5 | Sample 6 |
| Immediately before the 1st exposure | $1.25 \times 10^{-2}$ | $5 \times 10^{-7}$ | $<10^2$ | $<10^2$ |
| 1st exposure | $1.25 \times 10^{-2}$ | $5 \times 10^{-7}$ | $<10^2$ | $4 \times 10^5$ |

TABLE 19-continued (samples 5 and 6)

|  | $OH^-$ concentration (mole/l) | | Germ concentration (number/ml) | |
| --- | --- | --- | --- | --- |
|  | Sample 5 | Sample 6 | Sample 5 | Sample 6 |
| 3 days after the 1st exposure: 2nd exposure | $1.25 \times 10^{-2}$ | $5 \times 10^{-7}$ | $<10^2$ | $9 \times 10^6$ |
| 4 days after the 2nd exposure | $1.25 \times 10^{-2}$ | $5 \times 10^{-7}$ | $<10^2$ | $6 \times 10^7$ |

These results illustrate the efficacy of the process according to the invention in its protective aspect.

TABLE 20

(samples 5 and 6)

|  | $OH^-$ concentration (mole/l) | | Brookfield ™ viscosity (mPa·s) | |
| --- | --- | --- | --- | --- |
|  | Sample 5 | Sample 6 | Sample 5 | Sample 6 |
| Immediately before the 1st exposure | $1.25 \times 10^{-2}$ | $5 \times 10^{-7}$ | 444 | 394 |
| 1 day after the 1st exposure | $1.25 \times 10^{-2}$ | $5 \times 10^{-7}$ | 518 | 463 |
| 5 days after the 1st exposure: 2nd exposure | $1.25 \times 10^{-2}$ | $5 \times 10^{-7}$ | 804 | 676 |
| 4 days after the 2nd exposure | $1.25 \times 10^{-2}$ | $5 \times 10^{-7}$ | 1150 | 855 |
| 26 days after the 1st exposure | $1.25 \times 10^{-2}$ | $5 \times 10^{-7}$ | 1907 | 1190 |
| 26 days after the 1st exposure and after 5 minutes of intense stirring | $1.25 \times 10^{-2}$ | $5 \times 10^{-7}$ | 565 | 444 |

Moreover, the Brookfield™ viscosities of the sample according to the invention are not degraded relative to the sample representing the prior art.

After 26 days, a part of sample 5 according to the invention having been subject to the previous exposures was treated through the introduction of gaseous $CO_2$, so as to reduce the $OH^-$ ion concentration to a value equal to $2 \times 10^{-6}$ mole/l.

This instant corresponds to the instant T=0 for this new sample.

This part of sample 5, henceforth called sample 5-2, and representing the invention, will be subjected to a certain number of exposures.

For sample 5-2, measurements of the $OH^-$ ion concentration (mol/l), of the number of microbial germs (number/grain), and of the Brookfield™ viscosity (mPa·s) will then be taken.

These results are shown in tables 21 and 22.

TABLE 21

(sample 5-2)

|  | $OH^-$ concentration (mole/l) | Germ concentration (number/ml) |
| --- | --- | --- |
| Immediately before the 1st exposure | $2 \times 10^{-6}$ | $<10^2$ |
| Exposure | $4 \times 10^{-6}$ | $2 \times 10^6$ |

These results demonstrate that the process according to the invention enabled the microbial germ concentration to be increased anew: the process according to the invention thus enables microbial growth in the aqueous suspension of mineral matter to be controlled.

TABLE 22

(sample 5-2)

| | $OH^-$ concentration (mole/l) | Brookfield™ viscosity (mPa·s) |
|---|---|---|
| Immediately before the $1^{st}$ exposure | $2 \times 10^{-6}$ | 638 |
| 1 day after the $1^{st}$ exposure | $2 \times 10^{-6}$ | 680 |
| 5 days after the $1^{st}$ exposure: $2^{nd}$ exposure | $3 \times 10^{-6}$ | 790 |
| 12 days after the $1^{st}$ exposure | $4 \times 10^{-6}$ | 948 |
| 26 days after the $2^{nd}$ exposure | $8 \times 10^{-6}$ | 1198 |
| 26 days after the $1^{st}$ exposure and after 5 minutes of intense stirring | $6 \times 10^{-6}$ | 688 |

Moreover, the Brookfield™ viscosities are not degraded relative to the sample representing the prior art.

Example 4

The aim of this example is to illustrate the process according to the invention, in its curative and protective modes, applied to an aqueous suspension of mineral matter which is kaolin, and in the event that the process according to the invention uses a biocide according to stage d) which is o-phenylphenol.

Its aim is also to illustrate that the process according to the invention allows the development of the growth of microbial germs to be controlled in such a suspension.

Pigment Suspension

An aqueous suspension containing 78.3% by dry weight of natural calcium carbonate which is marble (of which 90% by weight of the particles have a diameter of less than 2 μm, and 65% by weight of the particles have a diameter of less than 1 μm), obtained by grinding, was prepared, using 0.65% by dry weight relative to the dry weight of mineral matter, of a commercially available polyacrylate neutralised by a sodium/magnesium mixture.

The pH value of the suspension after grinding was 9.7, measured at 20° C.

2 samples of 1 kg were prepared from the pigment suspension.

Microbial Suspension

A mixture, formed from 7 types of different gram-negative bacteria, was prepared, mostly comprised according to the family of pseudomonads (for the most part *Pseudomonas aeruginosa*), isolated from calcium carbonate suspensions having germinated naturally, originating from Austria.

The 7 different varieties of microbes were able to be identified using the API™ test which is well known to the skilled man in the art, and developed by the company BIOMERIEUX™.

The microbe concentration is $5 \times 10^6$ germs/ml.

Sample 7

This sample is used to illustrate the process according to the invention in its curative mode, and in combination with a biocide which is o-phenylphenol.

This sample according to the invention corresponding to 1 kg of the said pigment suspension was mixed under stirring in 10 ml of microbial suspension and then incubated for 7 days at 32° C. in an incubation oven.

The bacterial concentration after one week's incubation was $2 \times 10^7$ germs/ml.

After this, 200 ppm of o-phenylphenol was added to the sample under substantial stirring, in the form of a 45% solution of o-phenylphenol, dissolved in a solution containing KOH at a concentration of 1.07 moles KOH per mole of o-phenylphenol. 1270 ppm of $Ca(OH)_2$ was also added as a finely ground suspension (the average diameter of the particles after grinding was 2 at a concentration of 2.7 molar $Ca(OH)_2$.

The Brookfield™ viscosity of the suspension of calcium carbonate immediately after addition of the CaO was 271 mPa·s.

This sample according to the invention was then mixed several times with 10 ml of microbial suspension, and then incubated each time in an incubation oven, for 24 hours at 30° C.

The $OH^-$ ion concentration (mol/l), microbial germs concentration (number/gram), and Brookfield™ viscosity (mPa·s) values were then determined.

These results are shown in tables 23 and 24.

TABLE 23

(sample 7)

| | $OH^-$ concentration (mole/l) | Germ concentration (number/ml) |
|---|---|---|
| 1 day after exposure | $1.58 \times 10^{-2}$ | $<10^2$ |
| 2 days after exposure | $1.58 \times 10^{-2}$ | $<10^2$ |
| 7 days after exposure | $1.58 \times 10^{-2}$ | $<10^2$ |

These results demonstrate that the process according to the invention enables a curative treatment of the aqueous suspension of mineral matter to be obtained.

TABLE 24

(sample 7)

| | $OH^-$ concentration (mole/l) | Brookfield™ viscosity (mPa·s) |
|---|---|---|
| Immediately before exposure | $1.58 \times 10^{-2}$ | 271 |
| 1 day after exposure | $1.58 \times 10^{-2}$ | 698 |
| 4 days after exposure | $1.58 \times 10^{-2}$ | 823 |
| 25 days after exposure | $1.58 \times 10^{-2}$ | 872 |
| 25 days after exposure and after 5 minutes of intense stirring | $1.58 \times 10^{-2}$ | 282 |

Moreover, the Brookfield™ viscosities of the aqueous suspension of mineral matter according to the invention are not degraded.

Sample 8

This sample is used to illustrate the prior art and uses a biocide which is o-phenylphenol.

The second sample according to the invention corresponding to 1 kg of the said pigment suspension was mixed under substantial stirring with 10 ml of microbial suspension and then incubated in an incubation oven for 7 days at 32° C.

The microbial concentration after one weeks incubation was $2 \times 10$ germs/ml.

200 ppm of o-phenylphenol was then added to this second sample under substantial stirring, in the form of a 45% solution of o-phenylphenol, dissolved by 1.07 mole of KOH per mole of o-phenylphenol.

The Brookfield™ viscosity immediately after the addition of o-phenylphenol was 285 mPa·s.

The OH⁻ ion concentration (mol/l) and microbial germs concentration (number/gram) values were then determined. These results are shown in table 27.

TABLE 27

(sample 8)

| | $OH^-$ concentration (mole/l) | Germ concentration (number/ml) |
|---|---|---|
| 1 day after exposure | $6.3 \times 10^{-5}$ | >$10^2$ |
| 2 days after exposure | $6.3 \times 10^{-5}$ | >$10^4$ |
| 7 days after exposure | $6.3 \times 10^{-5}$ | >$10^5$ |

Sample 8, representing the prior art, shows that the o-phenylphenol presents an insufficient microbicidal effect, in relation to the germs used in the curative range.

Preservation is incomplete and is not sufficient. Conversely, with sample 7 according to the invention, it was possible to show that the process according to the invention which combines the use of o-phenylphenol and a stage of increase of the OH⁻ ion concentration enables very satisfactory results to be obtained in respect of the reduction of microbial germs in the aqueous suspension of mineral matter.

Example 5

The aim of this example is to illustrate the process according to the invention in its curative and protective modes in relation to wagon washing water.
Preservation of Wagon Washing Water
in order to simulate wagon washing water, a buffered kitchen salt solution was used, comprising 3% by weight of a suspension of calcium carbonate, taken from example 1.

The disinfection test was then undertaken on two different samples.
Sample 9

This sample is used to illustrate the process according to the invention in its protective mode.

The Ca(OH) was dissolved in a buffered solution of sterile phosphate at 0.85% by weight (PBS) and was mixed after 24 hours' storage at 30° C. with the bacteria/yeasts cocktail indicated in table 28.

The samples were incubated once more for 24 hours at 30° C. and then removed from the plates.

The germs which had grown were examined under an optical microscope.
Sample 10

This sample is used to illustrate the process according to the invention in its curative mode.

A cocktail of bacteria (in PBS), firstly, and a bacteria/yeasts cocktail in (PBS), secondly, were mixed with Ca(OH)₂, stored, and then removed from their moulds.

TABLE 28

(Composition of microbe cocktail)

| Type of bacteria | Observations |
|---|---|
| Bacteria cocktail without yeast: | |
| *Pseudomonas aeruginosa* | Gram-negative, not Enterobacteriacae |
| *Pseudomonas Pseudoalcaligenes* | Gram-negative, not Enterobacteriacae |
| *Pseudomonas stuzeri* | Gram-negative, not Enterobacteriacae |
| *Acinetobacter baumannii/calco* | Gram-negative, enterobacteriacae |
| *Klebsiella* spp. | Gram-negative, enterobacteriacae |
| *Bazillus subtilis* | Gram-positive, former of spores |
| *Bazillus* spp. | Gram-positive, |
| *Staphylococcus cohnii cohnii* | Gram-positive, |
| *Koc. Varians/rosea* | Gram-positive, |
| *Micrococcus kristae* | Gram-positive, |
| "Yeasts" and others: | |
| *Candida albicans*, eucaryote, monocellular with strong growth | Yeast |
| Rosa Germ isolated from a solution of sodium polyacrylate, resistant to formaldehyde | not specified in greater detail |
| Rosarot Germ isolated from a paper machine circuit, a germ with an unstable gram value | not specified in detail |

Tables 29 and 30 indicate the OH⁻ ion concentration (mole/l) and the yeast germ concentration (number/ml) measured in the samples, after 24-hours' incubation, for different initial concentrations of Ca(OH)₂.

TABLE 29

(sample 9)

| | 0 ppm | 200 ppm [1] | 500 ppm [1] | 1000 ppm [1] | 2000 ppm [1] |
|---|---|---|---|---|---|
| microbial germs concentration (number/ml) | $10^3$ | $10^3$ | 30 | <10 | <10 |
| $OH^-$ ion concentration (mole/l) | $3 \times 10^{-7}$ | $5 \times 10^{-4}$ | $3 \times 10^{-3}$ | $1 \times 10^{-2}$ | $5 \times 10^{-2}$ |

[1] Dosage of Ca(OH)₂: Active quantity/Global

TABLE 30

(sample 10)

| | 0 ppm | 200 ppm [1] | 500 ppm [1] | 1000 ppm [1] |
|---|---|---|---|---|
| microbial germs (number/ml) | $10^5$ | $10^5$ | 30 | <10 |
| $OH^-$ ion concentration (mole/l) | $3 \times 10^{-7}$ | $4 \times 10^{-5}$ | $3 \times 10^{-3}$ | $1 \times 10^{-2}$ |

[1] Dosage of Ca(OH)₂: Active quantity/Global

Thus, table 29 demonstrates that for an initial Ca(OH)₂ concentration of 200 ppm, after 24-hour a microbial germ concentration of 1000/ml is obtained, and an OH⁻ ion concentration of $5 \times 10^{-4}$ mole/l.

The value of the microbial germ concentration was reduced to 50/ml, for an initial Ca(OH)₂ concentration of 500 ppm; an OH⁻ ion concentration of $3 \times 10^{-3}$ mole/l is then obtained.

These results indeed demonstrate the protective effect of the process according to the invention.

Finally, the value of the microbial germ concentration is reduced to a quantity less than 10/ml, for an initial Ca(OH)₂ concentration of 500 ppm; an OH⁻ ion concentration of $3 \times 10^{-3}$ mole/l is then obtained.

This latter result illustrates the fact that with the process according to the invention used in its protective mode it is possible to obtain aqueous suspensions of mineral matter with a very low quantity of microbial germs, notably a quantity of less than 10 per ml.

At the same time, table 30 demonstrates the efficacy of the process according to the invention in its curative mode since, after 24 hours, the microbe concentration is reduced particularly if the initial $Ca(OH)_2$ concentration is substantial.

It is thus noted that with an initial $Ca(OH)_2$ concentration of 1000 ppm, a very large part of the microbial germs is destroyed since their concentration is less than 10 per ml after 24 hours.

This latter result illustrates the fact that with the process according to the invention used in its curative mode it is possible to obtain aqueous suspensions of mineral matter with a very low quantity of microbial germs, notably a quantity of less than 10 per ml.

Samples 9 and 10 of initial $Ca(OH)_2$ concentration equal to 1000 ppm were then removed from their mould at 30° C. on to a bacterial medium called a PCA (Plate Count Agar).

It is indicated that these media correspond to a bacterial formulation described in the following works: "American Public Health Association: Standard Methods for the Examination of Dairy Products, 15th ed., 1985", "American Public Health Association, American Water Works Association and Water Pollution Control Federation: Standard Methods for the Examination of Water and Wastewater, 20th ed., Washington, 1998" and "An improved agar medium for the detection of proteolytic organisms in total bacterial counts, J. Appl, Bact., 33; 363-370 (1970)".

After 48 hours' incubation, the samples are once again removed from their moulds on to the same medium of type PCA.

In terms of microbial germs, fewer than 40 bacteria per ml are counted, and fewer than 100 microbes other than bacteria per ml.

These results thus illustrate the efficacy of the process according to the invention in its curative mode.

For a part of sample 9, named 9-2, the $OH^-$ ion concentration was reduced to a value of $5 \times 10^{-7}$ mole/l by the addition of gaseous $CO_2$. It was incubated once again for 24 hours in the presence of the cocktail of bacteria and yeasts described in table 28. It was then removed from its mould on to a bacterial medium of type PCA, as described previously.

As previously, the microbial germ concentration as a function of the initial $Ca(OH)_2$ concentration was then measured: these results are shown in table 31.

TABLE 31

| (sample 9-2) | | | |
|---|---|---|---|
| | 0 ppm | 200 ppm [1] | 1000 ppm [1] |
| microbial germ concentration (number/ml) | >$10^4$ | >$10^5$ | >$10^5$ |
| $OH^-$ ion concentration (mole/l) | $1 \times 10^{-6}$ | $1 \times 10^{-6}$ | $1 \times 10^{-6}$ |

[1] Dosage of $Ca(OH)_2$: Active quantity/Global

These results demonstrate that by reducing the $OH^-$ ion concentration through the addition of liquid $CO_2$ it was possible, using the process according to the invention, to cancel the protective effect and restart microbial growth.

Example 6

This example illustrates the process according to the invention in which the stage of reduction of the $OH^-$ ion concentration is combined with a physical process, which in this case is a process based on increasing the temperature.

Pigment Suspension

An aqueous suspension containing OA % by dry weight of natural calcium carbonate which is marble (of which 90% by weight of the particles have a diameter of less than 2 μm, and 65% by weight of the particles have a diameter of less than 1 μm), obtained by grinding, was prepared, using 0.65% by dry weight relative to the dry weight of mineral matter, of a commercially available polyacrylate neutralised by a sodium/magnesium mixture.

2 samples were prepared each time.

Microbe Suspension

A microbe suspension of concentration equal to $10^4$ microbes/g, the composition of which is given by table 32, was prepared.

Sample 11

This sample illustrates the invention and consists of a pigment suspension, in which the microbe suspension was mixed, and into which a solution containing 500 ppm of $Ca(OH)_2$ was introduced.

This sample was incubated for 24 hours at 20° C.

Sample 12

This sample illustrates the prior art and is identical to sample 11, except that it does not contain $Ca(OH)_2$.

This sample was incubated fix 24 hours at 20° C.

Sample 13

This sample illustrates the invention and consists of a pigment suspension, in which the microbe suspension was mixed, and into which a solution containing 500 ppm of $Ca(OH)_2$ was introduced.

This sample was incubated for 24 hours at 40° C.

Sample 14

This sample illustrates the prior art and is identical to sample 13, except that it does not contain $Ca(OH)_2$.

This sample was incubated for 24 hours at 40° C.

TABLE 32

| (composition of microbe cocktail) | |
|---|---|
| Type of bacteria | Observations |
| Bacteria cocktail without yeast: | |
| *Pseudomonas aeruginosa* | Gram-negative, not Enterobacteriacae |
| *Pseudomonas Pseudoalcaligenes* | Gram-negative, not Enterobacteriacae |
| *Pseudomonas stuzeri* | Gram-negative, not Enterobacteriacae |
| *Acinetobacter baumannii/calco* | Gram-negative, enterobacteriacae |
| *Klebsiella* spp. | Gram-negative, enterobacteriacae |
| *Bazillus subtilis* | Gram-positive, former of spores |
| *Bazillus* spp. | Gram-positive, |
| *Staphylococcus cohnii* | Gram-positive, |
| *Koc. Varians/rosea* | Gram-positive, |
| *Micrococcus kristae* | Gram-positive, |
| "Yeasts" and others: | |
| *Candida albicans*, eucaryote, monocellular with high growth | Yeast |
| Rosa Germ isolated from solution of sodium polyacrylate, resistant to formaldehyde | not specified in greater detail |
| Rosarot Germ isolated from a paper machine circuit, a germ with an unstable gram value | not specified in detail |

For each sample the $OH^-$ ion concentration (mole/l) was measured, together with the bacteria concentration and the concentration in microbes other than bacteria (number/ml); these results are shown in table 33.

TABLE 33

|  | Sample 12 | Sample 14 | Sample 11 | Sample 13 |
|---|---|---|---|---|
| Temperature | 20° C. | 40° C. | 20° C. | 40° C. |
| Initial Ca(OH)$_2$ concentration (ppm) | 0 | 500 | 0 | 500 |
| Bacteria concentration (number/ml) | >10$^4$ | >10$^4$ | 2 × 10$^4$ | <10 |
| Concentration in microbes other than bacteria (number/ml) | >10$^4$ | >10$^4$ | 2 × 10$^3$ | <10 |
| OH$^-$ ion concentration (mole/l) | 2 × 10$^{-7}$ | 2 × 10$^{-7}$ | 3 × 10$^{-3}$ | 3 × 10$^{-3}$ |

Table 33 demonstrates that the stage of reduction of the OH$^-$ ion concentration, which is representative of the process according to the invention, allows, at 20° C., the number of microbial germs of all types to be reduced (sample 11).

It also demonstrates that this stage of reduction of the OH$^-$ ion concentration, in combination with a physical process which is an increase of the temperature to 40° C., the said combination also being representative of the process according to the invention, enables the concentration in microbes of all types to be reduced in very marked fashion, since this concentration is then less than 10 per ml.

For samples 11 and 13 according to the invention, the OH$^-$ ion concentration was then reduced to a value of 3.2×10$^{-6}$ mole/l through the addition of CO$_2$. These samples were then once again incubated in the microbial cocktail described above, and then removed from their moulds on to a microbial cocktail of type PCA at 30° C., and the said cocktail was left to act for 24 hours.

The OH$^-$ ion concentration is then equal to 1×10$^{-4}$ mole/l and a new increase of the microbial germs is then observed: by means of the process according to the invention, it was thus possible to restart the microbial growth.

Example 7

The aim of this example is to illustrate the process according to the invention, in its curative mode by grinding, applied to an aqueous suspension of mineral matter which is calcium carbonate.

Its aim is also to illustrate that the process according to the invention allows the development of the growth of microbial germs to be controlled in such a suspension, without modifying its stability in terms of Brookfield™ viscosity.

Microbial Suspension

A mixture of 7 types of different gram-negative bacteria was prepared, mostly comprised according to the family of pseudomonads (for the most part *pseudomonas aeruginosa*), isolated from a calcium carbonate slurry seeded naturally with germs, originating from Austria.

The 7 different varieties of microbes were able to be identified using the API™ test which is well known to the skilled man in the art, and developed by the company BIOMERIEUX™.

The microbe concentration is 5×10$^6$ germs/ml.

Sample 15

This sample is used to illustrate the prior art; it is obtained by exposure of a suspension of calcium carbonate to the microbial suspension, then by grinding of the said suspension of calcium carbonate.

5 kg of dry calcium carbonate was prepared, from an aqueous suspension of 77.3% by dry weight of natural marble (of which 30% by weight of the particles have a diameter of less than 2 μm, and 8% by weight of the particles have a diameter of less than 1 μm).

The said suspension was treated with 10 ml of the microbial suspension and stored for 24 hours at 30° C.

By grinding with 0.65% by dry weight relative to the dry weight of mineral matter of a polyacrylate neutralised by a commercially available mixture of sodium and magnesium, a suspension was produced in which 88% by weight of the particles have a diameter of less than 2 μm, and 64% by weight of the particles have a diameter of less than 1 μm.

The pH value of the suspension after grinding was 9.7 measured at 20° C.

The Brookfield™ viscosity 24 hours after grinding was 284 mPa·s.

The microbial germ concentration of this suspension after grinding was greater than 10$^{-5}$ germs/ml.

Sample 16

This sample is used to rate the treatment according to the invention, in its protective mode.

5 kg of dry calcium carbonate was prepared, from an aqueous suspension of 77.1% by weight of natural marble (of which 30% by weight of the particles have a diameter of less than 2 μm, and 8% by weight of the particles have a diameter of less than 1 μm).

The said suspension was treated with 10 ml of the microbial suspension and stored for 24 hours at 30° C.

After this, this sample was mixed under substantial stirring, in a solution of ground Ca(OH)$_2$ (with the average diameter of the particles being equal to 2 μm) containing 2×10$^{-2}$ mole/l of OH$^-$ ions.

By grinding with 0.65% by dry weight relative to the dry weight of mineral matter of a polyacrylate neutralised by a commercially available mixture of sodium and magnesium, a suspension was produced in which 91% by weight of the particles have a diameter of less than 2 μm, and 66% by weight of the particles have a diameter of less than 1 μm.

The value of the suspension after grinding was 12.2 measured at 20° C.

The Brookfield™ viscosity measured 24 hours after the previous addition was 253 mPa·s.

The germ concentration of this suspension after grinding was less than 10$^2$ germs/ml.

These results demonstrate that the process according to the invention has enabled the microbial contamination of the sample to be reduced very clearly relative to the treatment of the prior art, without however modifying the stability of the sample according to the invention in terms of Brookfield™ viscosity.

After 2 days, sample 16 according to the invention was treated through the introduction of gaseous CO$_2$, so as to reduce the OH$^-$ ion concentration to a value equal to 2×10$^{-5}$ mole/l.

The Brookfield™ viscosity 24 hours after the previous addition of CO$_2$ was 222 mPa·s.

The germ concentration of this suspension after grinding was less than 10$^2$ germs/ml.

Subsequently, sample 16 according to the invention was again treated by the introduction of gaseous CO$_2$.

It was then treated with 1 ml of microbial suspension and stored at 30° for 48 hours. The germ concentration of this suspension was then greater than 10$^6$ germs/ml. These results demonstrate that the process according to the invention, through the addition of gaseous CO$_2$, enabled the microbial growth to be stimulated in the sample.

Example 8

The aim of this example is to illustrate the process according to the invention, in its curative mode, applied to an aqueous suspension of mineral matter which is a precipitated calcium carbonate.

Its aim is also to illustrate that the process according to the invention allows the development of the growth of microbial genus to be controlled in such a suspension.

Pigment Suspension:

An aqueous suspension was manufactured containing 50.0% by dry weight of carbonate precipitate of the Syncarb™ F 474 type, sold by the company OMYA™. The pH value of the suspension was 9.7 measured at 20° C.

2 samples of 1 kg were prepared from the pigment suspension.

Bacterial Suspension:

A mixture of 7 different types of bacteria was produced, which were gram-negatives, mainly formed from the family of pseudomonads (the majority being *Pseudomonas aeruginosa*), isolated from a suspension of calcium carbonate having germinated naturally, originating from Austria.

The germ concentration is $2 \times 10^5$ germs/ml.

Sample 17

The first sample of 1 kg of suspension of precipitated calcium carbonate was mixed under vigorous stirring with 0.075 mole of $OH^-$ ions (added in the form of a 2.7 molar suspension of $Ca(OH)_2$ in water).

The viscosity of the suspension of precipitated calcium carbonate immediately after addition of the $Ca(OH)_2$ was equal to 227 mPa·s.

The pH of the suspension was equal to 12.1.

This suspension now corresponds to sample 17 which illustrates the invention.

Sample 18

The other 1 kg sample of precipitated calcium carbonate suspension was mixed with the bacterial suspension.

The viscosity of this suspension was equal to 257 mPa·s.

This suspension now corresponds to sample 18 which illustrates the prior art.

Samples 17 and 18 were then subjected to a number of exposures, as indicated in table 34. The $OH^-$ ion concentration was determined for each of them, together with the microbial germ concentration at different times (according to the previously described methods), as also indicated in table 34.

TABLE 34

| Time (T = number of days) | Event (Exposure and/or measurements) | $OH^-$ concentration (mole/l) | | Germ concentration (number/ml) | |
|---|---|---|---|---|---|
| | | Sample 17 | Sample 18 | Sample 17 | Sample 18 |
| T = 0 | Measurements | $2 \times 10^{-2}$ | $7.5 \times 10^{-5}$ | $<10^2$ | $3.3\ 10^4$ |
| T = 2 | Exposure and measurements | $2 \times 10^{-2}$ | $1 \times 10^{-4}$ | $<10^2$ | $>10^5$ |
| T = 4 | Exposure and measurements | $2 \times 10^{-2}$ | $1 \times 10^{-4}$ | $<10^2$ | $>>10^5$ |

These results illustrate the efficacy of the process according to the invention in its protective aspect.

In addition, the viscosities of sample no 17 according to the invention measured at T=2 days and T=4 days are equal to 227 mPa·s and 232 mPa·s: they are thus not degraded compared to the sample representing the prior art.

After 4 days, a part of sample 17 according to the invention was treated through the introduction of gaseous $CO_2$, so as to reduce the $OH^-$ ion concentration to a value of $4 \times 10^{-6}$ mole/litre.

This part of sample 17 is henceforth called sample 17b.

This sample 17b was then subjected to a number of exposures, as indicated in table 35.

The $OH^-$ ion concentration was then determined, together with the microbial germ concentration at different times (according to the previously described methods), as indicated in table 35 (instant T=0 corresponds to the time of introduction of gaseous $CO_2$ into sample 17, henceforth called sample 17b).

TABLE 35

| Time (T = number of days) | Event (exposure and/or measurements) | $OH^-$ concentration (mole/litre) | Germ concentration (number/ml) |
|---|---|---|---|
| T = 0 | Measurements | $4 \times 10^{-6}$ | $<10^2$ |
| T = 2 days | Exposure Measurements | $4 \times 10^{-6}$ | $2.7\ 10^3$ |
| T = 4 days | Exposure Measurements | $4 \times 10^{-6}$ | $>10^5$ |

These results demonstrate that the process according to the invention enabled the germ concentration to be increased anew: the process according to the invention thus enables microbial growth in the aqueous suspension of precipitated calcium carbonate to be controlled.

The invention claimed is:

1. An aqueous suspension of mineral matter comprising calcium carbonate, at least one dispersing agent, and an antimicrobial agent consisting of one or more $OH^-$ ion donors selected from alkali oxides and alkali hydroxides, wherein the aqueous suspension is obtained by a process for disinfecting or preserving the aqueous suspension of or from microbial contamination, wherein the process comprises:
    a) at least one stage to increase and maintain the $OH^-$ ion concentration of the aqueous suspension of the mineral matter comprising calcium carbonate, to a value greater than or equal to $1 \times 10^{-2}$ mole/l, by addition of the antimicrobial agent consisting of one or more $OH^-$ ion donors selected from alkali oxides and alkali hydroxides, for a sufficient time to disinfect or preserve the aqueous suspension of the mineral matter comprising calcium carbonate of or from microbial contamination, and
    b) at least one stage of dispersion and/or grinding of the aqueous suspension of the mineral matter comprising calcium carbonate, occurring before, during or after stage a),
    wherein the aqueous suspension of mineral matter has a microbe concentration of less than or equal to 100 microbes/gram.

2. The aqueous suspension according to claim 1, wherein the $OH^-$ ion concentration value in stage a) is higher than or equal to $2 \times 10^{-2}$ mole/l.

3. The aqueous suspension according to claim 1, wherein the one or more $OH^-$ ion donors added in stage a) is an alkali oxide.

4. The aqueous suspension according to claim 1, wherein the one or more $OH^-$ ion donors added in stage a) is an alkali hydroxide.

5. The aqueous suspension according to claim 1, wherein the one or more $OH^-$ ion donors added in stage a) is NaOH.

6. The aqueous suspension according to claim 1, wherein stage b) is conducted using at least one dispersing agent or at least one grinding aid agent.

7. The aqueous suspension according to claim 1, wherein a physical decontamination is introduced before, during or after stage a), and/or b).

8. The aqueous suspension according to claim 7, wherein the physical decontamination uses at least one treatment process based on an increase of temperature.

9. The aqueous suspension according to claim 1, wherein the mineral matter is natural and/or precipitated calcium carbonate.

10. The aqueous suspension according to claim 1, wherein the mineral matter is natural calcium carbonate.

11. The aqueous suspension according to claim 1, wherein the mineral matter is marble, calcite, chalk or their mixtures.

12. A paper formulation comprising or manufactured with the suspension according to claim 1.

13. A sheet of paper comprising or manufactured with the suspension according to claim 1.

14. A coating color comprising or manufactured with the suspension according to claim 1.

15. A water-based paint comprising or manufactured with the suspension according to claim 1.

16. A lacquer comprising or manufactured with the suspension according to claim 1.

17. A varnish comprising or manufactured with the suspension according to claim 1.

* * * * *